United States Patent [19]

Zalesky et al.

[11] Patent Number: 5,389,078
[45] Date of Patent: Feb. 14, 1995

[54] PROGRAMMABLE INFUSION PUMP FOR ADMINISTERING MEDICATION TO PATIENTS

[75] Inventors: Larry R. Zalesky, Blaine; Linda S. Hansen, Minnetonka, both of Minn.

[73] Assignee: SIMS Deltec, Inc., St. Paul, Minn.

[21] Appl. No.: 132,585

[22] Filed: Oct. 6, 1993

[51] Int. Cl.$^6$ .......................... A61M 1/00; A61M 5/00
[52] U.S. Cl. ................................... 604/151; 604/246; 128/DIG. 12; 128/DIG. 13
[58] Field of Search .................. 604/65, 67, 151–155, 604/246; 128/DIG. 1, DIG. 12, DIG. 13

[56] References Cited

U.S. PATENT DOCUMENTS

| | | | |
|---|---|---|---|
| 4,077,405 | 3/1978 | Haerten et al. | 128/DIG. 13 |
| 4,258,711 | 3/1981 | Tucker et al. | 128/DIG. 12 |
| 4,270,532 | 6/1981 | Franetzki et al. | |
| 4,411,651 | 10/1983 | Schulman | 604/151 |
| 4,469,481 | 9/1984 | Kobayashi | 128/DIG. 12 |
| 4,559,037 | 12/1985 | Franetzki et al. | 604/151 |
| 4,601,707 | 7/1986 | Albisser et al. | 604/151 |
| 4,624,661 | 11/1986 | Arimond | |
| 4,662,872 | 5/1987 | Cané | 128/DIG. 1 |
| 4,776,842 | 10/1988 | Franetzki et al. | 604/67 |
| 4,785,799 | 11/1988 | Schoon et al. | |
| 4,943,279 | 7/1990 | Samiotes et al. | 128/DIG. 13 |
| 5,010,473 | 4/1991 | Jacobs | |
| 5,049,141 | 9/1991 | Olive | 128/DIG. 12 |
| 5,181,910 | 1/1993 | Scanlon | |
| 5,256,157 | 10/1993 | Samiotes et al. | 128/DIG. 13 |

OTHER PUBLICATIONS

*Provider® One Instruction Manual*, Pancretec Inc. (undated).

*CADD-Micro TM Ambulatory Infusion Pump-Model 5900 Operator's Manual*, Pharmacia Deltec, Jul. 16, 1993.

*Primary Examiner*—C. Fred Rosenbaum
*Assistant Examiner*—Mark Bockelman
*Attorney, Agent, or Firm*—Merchant, Gould, Smith, Edell, Welter, & Schmidt

[57] ABSTRACT

A programmable infusion pump which combines automatic and demand doses of medication with any basal rates on a real-time basis to determine an effective rate at anytime during the delivery cycle without underdelivering fluid due to the minimum increment of fluid delivery by the pump.

18 Claims, 7 Drawing Sheets

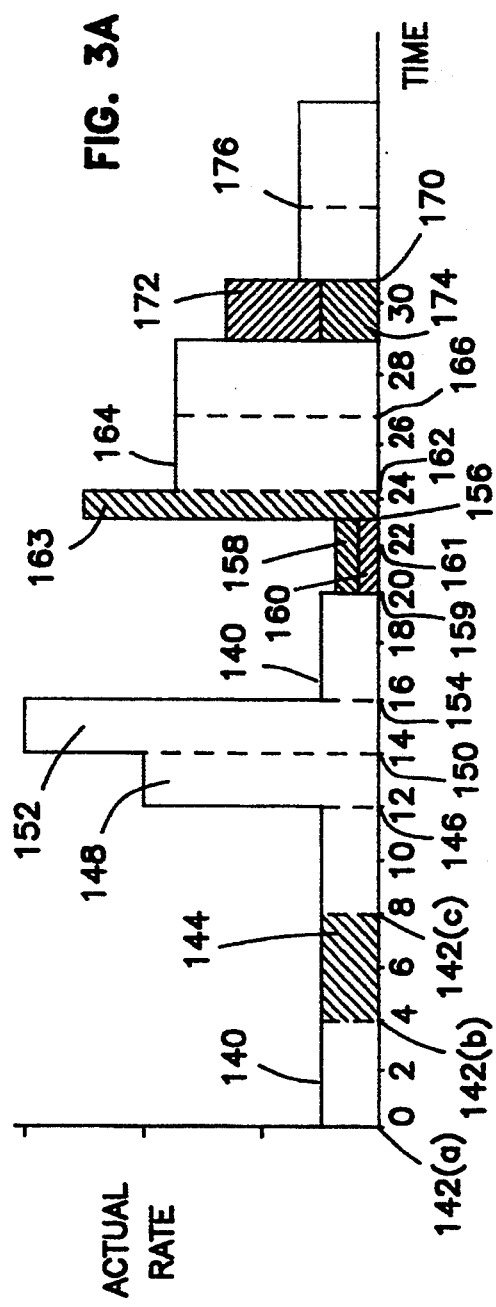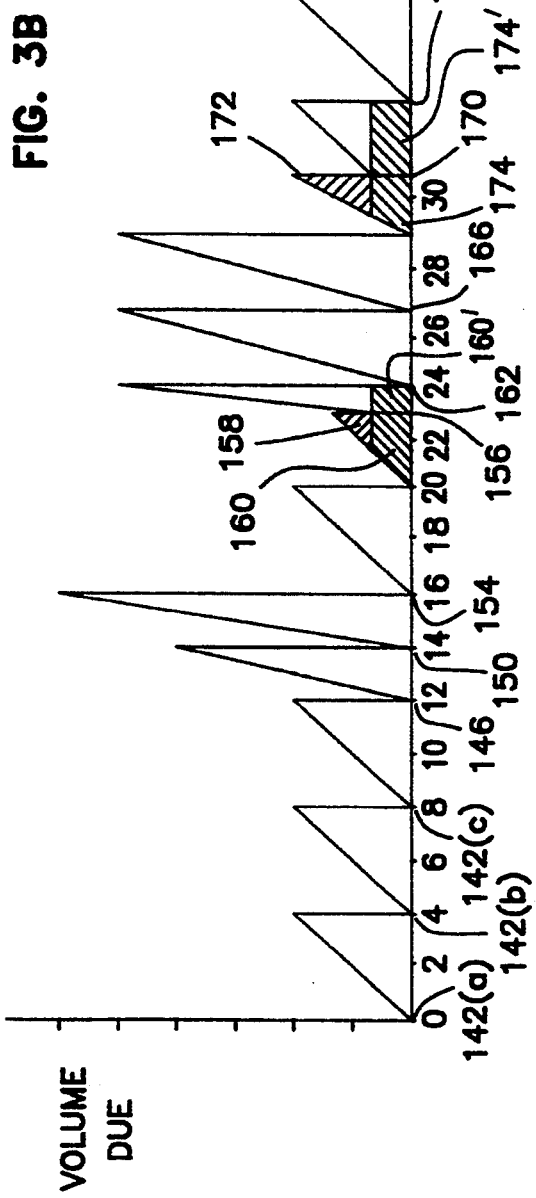

5,389,078

PROGRAMMABLE INFUSION PUMP FOR ADMINISTERING MEDICATION TO PATIENTS

FIELD OF THE INVENTION

The present invention is directed to a programmable infusion pump for administering medication to patients, and more particularly, to a programmable infusion pump which combines automatic and demand doses of medication with any basal rate on a real-time basis to determine an effective rate at any time during the delivery cycle without under-delivering fluid due to the minimum increment of fluid delivery by the pump.

BACKGROUND OF THE INVENTION

Some types of drug therapy are best administered continuously, rather than at fixed intervals. Ambulatory drug delivery provides patients with continuous drug therapy without hospitalization or otherwise being immobilized.

Measured drug therapy utilizes some combination of the following three options: continuous infusion, patient activated demand doses, and programmed automatic doses. For example, insulin may be delivered to a diabetic at a low continuous rate throughout the day, with programmed automatic dose increases proximate to mealtime. In another example, pain medication may be delivered to a patient at a continuous rate throughout the day, while allowing patient activated demand doses as needed. However, because over-delivery or under-delivery of the selected medication may be fatal to the patient, it is essential that the infusion pump accurately determines the amount of medication due to the patient on a real-time basis.

As a practical matter, infusion pumps deliver a fixed quantity of fluid, known as a stroke volume, for each pump activation. The stroke volume corresponds to the minimum quantity of fluid the pump can deliver for each activation. Only whole multiples of the stroke volume can be delivered. Fluid delivery is typically measured by determining the amount of fluid delivered per pump activation (stroke volume) and adjusting the interval between pump activations to alter the rate of fluid delivery.

For purposes of measured drug therapy, the time interval between pump activations can be several minutes. Accurate and timely drug delivery is complicated when a demand or automatic dose is called for between pump activations. In particular, the quantity of medication due for the period from the last pump activation to the demand or automatic dose must be calculated and incorporated into the new delivery rate. However, this quantity of medication due is seldom an even multiple of the stroke volume of the pump. Generally, the undelivered quantity of fluid comprises some even multiple of stroke volumes, plus some remainder which is less than the minimum amount of medication that can be delivered by one pump activation.

Another difficulty with ambulatory drug therapy is that the therapy is most effective when the patient has some degree of control and responsibility for the treatment. Therefore, a programmable drug infusion pump requires various safety features to maximize the flexibility to the patient without allowing the patient to alter operation parameters in a manner which could be dangerous or counter-productive to the drug therapy.

SUMMARY OF THE INVENTION

The present invention provides a method and system for administering fluid to a patient at multiple programmable rates without under-delivering fluid due to the minimum increment of fluid delivery permitted by the pump.

The programmable infusion pump combines automatic and demand doses of medication with any basal rate on a real-time basis to determine an effective rate for accurately delivering medication proximate the scheduled delivery time.

The programmable infusion pump has a motor with a stroke volume corresponding to a discreet volume of medication for each pump activation. The user may input a basal infusion rate corresponding to the time interval between basal pump activations, an automatic dose having a start time, a dose volume and a duration, and a demand dose having a start time, a demand dose volume and a duration. An effective rate corresponding to the time interval between pump activations is calculated which comprises the sum of the basal rate and any automatic and demand dose rates. Any undelivered volume of fluid which is scheduled for delivery prior to the start time of the effective rate is determined, and the undelivered volume of fluid corresponding to a whole number of stroke volumes is delivered to the patient. The undelivered volume of fluid which is a fraction of the stroke of volume is delivered by altering at least one of the time intervals at the effective rate.

In the preferred embodiment, the portion of undelivered fluid which is a fraction of the stroke volume is delivered after the undelivered fluid corresponding to the whole number of stroke volumes is delivered, so that the medication is delivered to the patient as close to the scheduled delivery time as possible.

BRIEF DESCRIPTION OF THE DRAWINGS

FIGS. 3A and 3B are a graphical illustration of an exemplary fluid delivery profile for both actual delivery rate and volume due.

DETAILED DESCRIPTION OF THE PREFERRED EMBODIMENT

The present computerized ambulatory drug delivery infusion pump provides measured drug therapy to patients in hospitals or out-patient settings. The infusion pump 10 preferably offers the capability for intravenous, intraarterial, subcutaneous, interperitoneal and epidural microinfusion. It is intended that the present invention is applicable to any infusion system which needs to accurately deliver a random combination of basal infusion rates, and automatic and demand doses. It will be understood by those skilled in the art that the infusion pump disclosed herein represents only an example of one type of pump suitable for use with the present invention.

Figure 1:
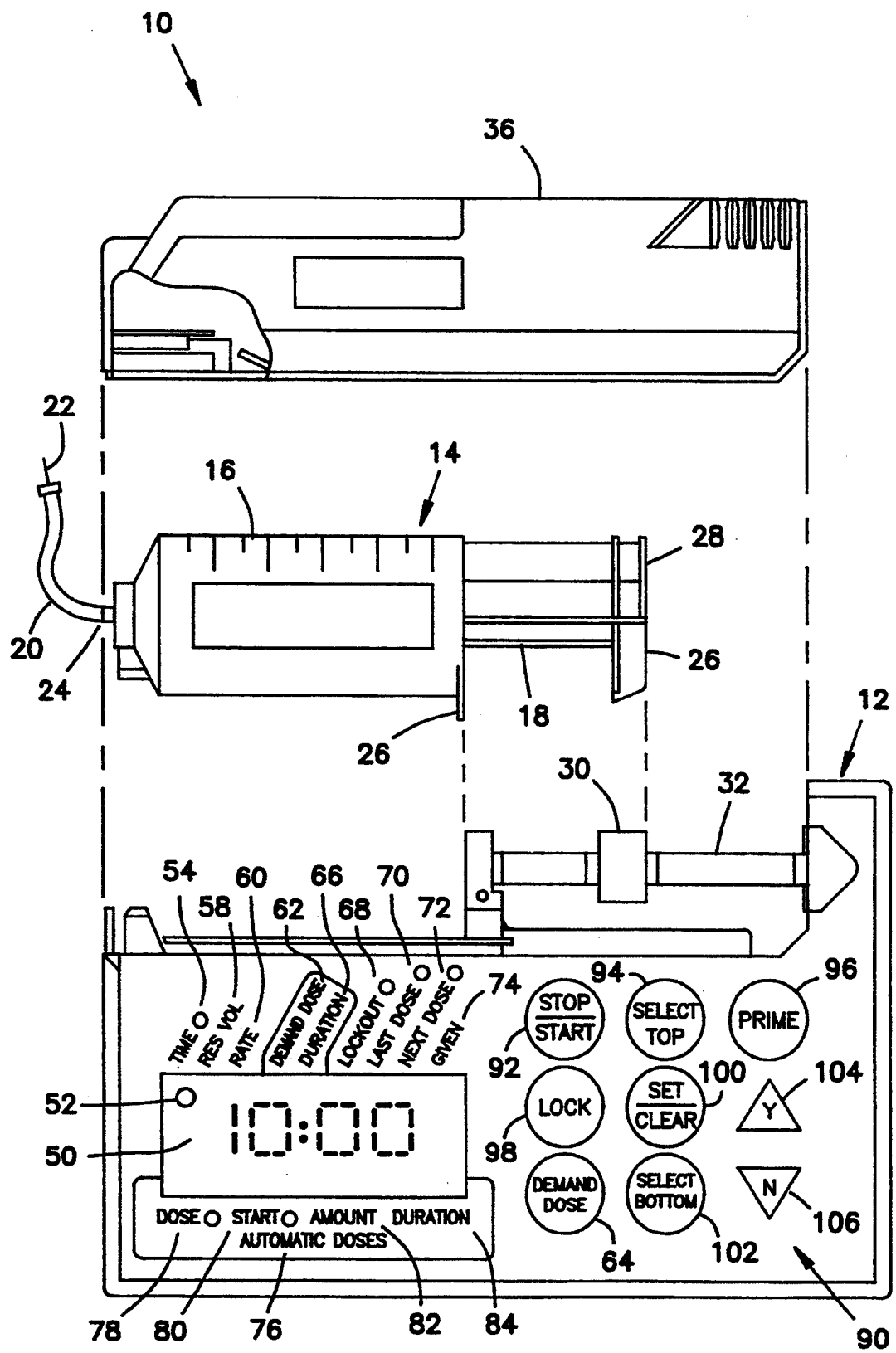
FIG. 1 illustrates an exploded view of the preferred computerized ambulatory drug delivery pump.

FIG. 1 illustrates the preferred infusion pump 10 having a pump controller 12 and a medication delivery system 14. The medication delivery system 14 has a medication reservoir 16 and a plunger 18. A fluid tubing 20 with a needle 22 is preferably attached to an opening 24 on the end of the medication reservoir 16. In the preferred embodiment, the medication reservoir 16 has a ten milliliter capacity.

The medication delivery system 14 preferably has a pair of reservoir tabs 26 for engaging with the pump controller 12. The end of the plunger 28 is preferably designed to engage with a drive nut 30 on a threaded drive shaft 32 on the pump controller 12. The threaded drive shaft 32 is preferably driven by a motor 34 (see FIG. 2) contained within the pump controller 12. When the medication delivery system 14 is engaged with the pump controller 12, a syringe cover 36 is attached to the pump controller 12 to enclose and protect the medication delivery system 14. A sensor 38 (see FIG. 2) is preferably provided on the pump controller 12 to determine whether the syringe cover 36 is securely attached to the pump controller 12. If the syringe cover 36 is not securely in place, the infusion pump 10 will signal an alarm and not make any deliveries.

The motor 34 is preferably monitored by shaft encoder 40. The shaft encoder 40 operates by shining an LED through a ten slot encoder disk attached to the shaft of the motor (not shown). A photo cell monitors the transition from dark to light and light to dark as the encoder disk rotates in front of the LED sensor. The output from the photo cell in the shaft encoder 40 is transmitted to microprocessor 120 to monitor medication delivery.

Each slot of the encoder disk corresponds to a discrete angular rotation of the threaded drive shaft 32, which translates to a predetermined linear movement of the drive nut 30 and the plunger 28. In the preferred embodiment, each slot in the encoder disk corresponds to the delivery of two micro liters of fluid. Therefore, the minimum stroke volume of the present infusion pump 10 corresponds to two micro liters of fluid delivered to the patient.

The operation of the exemplary pump 10 discussed below is set forth in a document entitled *CADD-Micro Ambulatory Infusion Pump, Model 5900 Operator's Manual*, dated Jul. 16, 1993, which is hereby incorporated by reference into this specification. The preferred infusion pump 10 has a display 50 which allows the user to input delivery variables and to monitor pump 10 operations. Labels along the top and bottom of the display 50 correspond to functions that are programmed into the pump or calculated by the pump. A cursor 52 indicates which function the user is programming at any given time.

The time function 54 corresponds to the current time of day according to the pump's internal real time clock 56. Res Vol 58 approximates the volume remaining in the medication reservoir 16. The volume remaining is calculated as the difference between the originally programmed reservoir volume and the volume of fluid that has been delivered. The pump 10 automatically recalculates this value when fluid is delivered or the fluid path is primed. Rate 60 is the programmed continuous rate of infusion in milliliters per hour. Demand dose 62 is a volume of medication in milliliters programmed to be delivered when demand dose key 64 is pressed. Duration 66 is the programmed length of time over which the demand dose is scheduled to be delivered. Lockout 68 is the minimum amount of time that is required to elapse between the start of one demand or automatic dose and the start of the next demand or automatic dose. Last dose 70 is the time the last automatic or demand dose started. Next dose 72 is the time the next scheduled automatic dose will begin. Given 74 is the total volume of medication delivered by the pump 10 since the last time this value was cleared, excluding fluid used to prime the fluid path.

A series of automatic dose functions 76 are listed along the bottom of the display 50. A dose number 78 is automatically assigned to each new automatic dose entered into the pump 10. Start time 80 is the time of day the automatic dose is programmed to begin. Amount 82 is the amount of medication in milliliters that is programmed to be delivered by the automatic dose. Duration 84 is the programmed length of time over which the automatic dose is scheduled to be delivered.

The keypad 90 is used for programming and operating the pump 10. The stop/start key 92 allows the user to start or stop the pump at any time. As will be discussed below, because the patient can stop the pump at random, it is essential that medication be delivered as close to the scheduled delivery time as possible. Otherwise, sudden termination of the pump can result in under delivery of medication.

The select top key 94 moves the pointer along the functions at the top of the display. The prime key 96 advances the plunger 18 in order to eliminate air from the fluid tubing 20 and to prepare the pump for delivery after attaching a new medication reservoir 16. The lock key 98 allows the user to view or change the current security lock level. A password corresponding to a series of key strokes is preferably included to prevent the patient from making ill-advised changes to the delivery schedule. The set clear key 100 is used to enter a new value into the pump's memory and to clear the Res Vol 58 value or the Given 74 value. The demand dose key 64 is used to deliver a demand dose. A dose counter in microprocessor 120 records the number and the time of demand doses that have been delivered. The select bottom key 102 moves the pointer along the automatic dose functions at the bottom of the display. The Y key 104 scrolls upward and the N key 106 scrolls downward.

Figure 2:
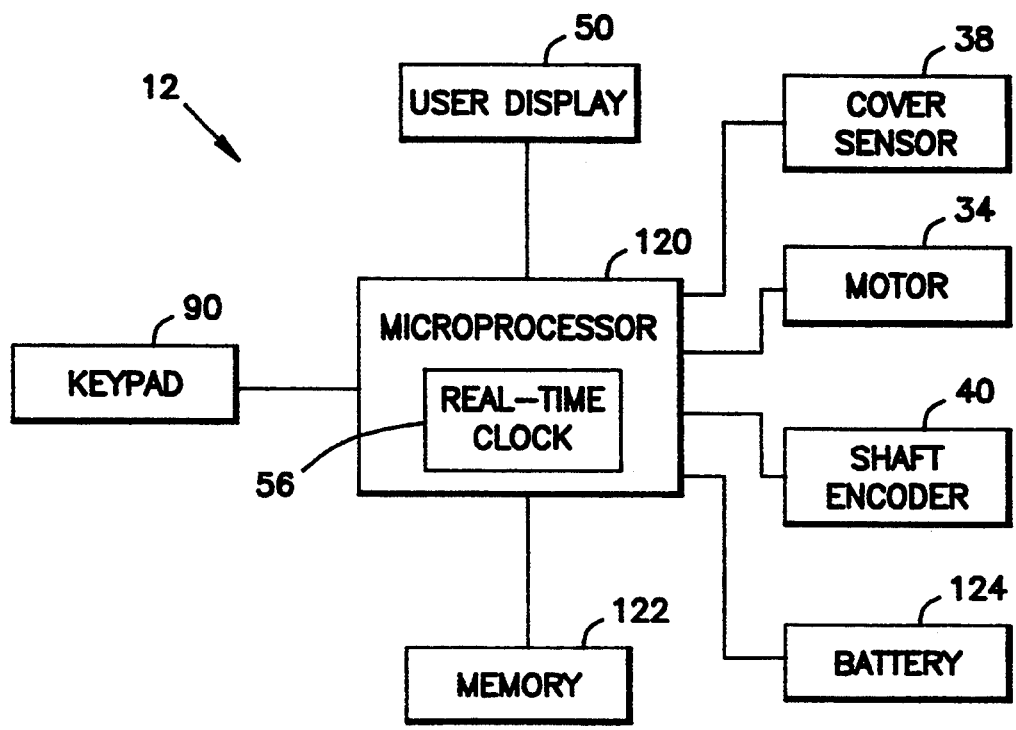
FIG. 2 is a schematic of the preferred pump controller for the pump of FIG. 1.

FIG. 2 is a schematic illustration of an exemplary embodiment of the pump controller 12. A microprocessor 120 is connected to a non-volatile memory element 122, which retains the system program and infusion parameters. A battery 124 provides power to all components of the pump controller 12.

In order to conserve power, the processor 120 spends most of the time in a stop mode. The keypad 90 and real time clock 56 wake the processor 120 from the stop mode when necessary. The keypad 90 wakes the processor 120 whenever any of the keys are pressed. The real time clock 56 wakes the processor 120 each second to provide handling for time delayed and periodic events.

Programming Options

The pump 10 offers three delivery options which may be used alone or in any combination: a continuous rate, a demand dose, and automatic doses. In addition, a lockout is provided which limits the frequency of demand and automatic doses.

A demand dose allows the patient to administer a programmed amount of medication as needed. Both the amount and the duration are preferably pre-programmed for the demand doses. Automatic dose may be pre-programmed to deliver doses at specific times of day. In the exemplary infusion pump 10, up to 24 automatic doses may be programmed, each with its own start time, amount, and duration. The pump 10 also has a lockout time which limits the frequency of doses. The lockout time is the minimum amount of time that is required to elapse between the start of one demand or automatic dose and the start of the next demand or automatic dose.

FIGS. 3A and 3B illustrates an exemplary delivery profile containing basal delivery rates, automatic doses and demand doses. FIG. 3A illustrates the Actual Rate vs. Time, where the vertical axis corresponds to rate (volume per unit time) and the horizontal axis corresponds to time. FIG. 3B illustrates Volume Due vs. Time for the same delivery profile, where the height of the triangular shapes corresponds to Volume Due at a given time. In particular, Volume Due accumulates linearly over time until a delivery is made, at which time the Volume Due drops.

Because FIGS. 3A and 3B correspond to the same delivery profile, the reference numerals for time dependent events are the same. In FIG. 3A, basal rate 140 is achieved by a series of pump activations at time intervals 142(a), 142(b), and 142(c). By calculating the area under the curve between any two pump activations, the volume of fluid delivered can be determined. For example, the area 144 between pump activations 142(b) and 142(c) corresponds to one half units of volume per four units of time for a total of two units of volume. Correspondingly, FIG. 3B illustrates two units of volume due at time intervals 142(a), 142(b), and 142(c).

A rate change at time 146 occurs precisely at the end of the prior delivery interval 142(c), so that there is no undelivered volume of fluid. Therefore, the rate change at time 146 corresponds to a simple step function to a new rate 148. It will be understood that the new rate 148 may be the result of either a demand dose or an automatic dose.

The dose 148 may, for example, correspond to two units of volume per two units of time for a total of four units of fluid. Correspondingly, FIG. 3B illustrates a total of four units of volume due at time interval 150.

Another rate change occurs at time 150 as a result of a demand or automatic dose 152. The dose was called for at a time when there was no undelivered volume of fluid, the demand or automatic dose 152 is also illustrated as a simple step function. Likewise, the rate decrease at time 154 corresponds to a simple step function reduction back to the basal rate 140.

It will be understood by those skilled in the art that while it would be possible to schedule automatic doses to occur precisely at the end of a previous infusion cycle, the availability of random demand doses makes such a calculation impossible. Furthermore, the first demand dose would disrupt the calculation for subsequent automatic doses. Therefore, demand and automatic doses will almost always occur at a time when there is some undelivered amount of fluid scheduled for delivery. Moreover, this undelivered amount of fluid will generally correspond to a number of whole pump activations (e.g. 2 micro-liter increments) and some remainder which is less than the minimum increment of fluid the pump is capable of delivering. For the basal rate 140 of FIG. 3A, the time at which the volume of fluid due corresponds to a number of whole pump activations occurs every two units of time. Therefore, a method and apparatus is required for making a real-time calculation of the effective rate at anytime during the delivery cycle, without under-delivering fluid due to the minimum increment of fluid delivery by the pump.

Rate change at time 156 occurs at a time which leaves an undelivered volume of fluid. The rate change, however, does not occur at a time corresponding to a number of whole pump activations (i.e. times 159, 161 or 162). Rather, it occurs between time 161 and time 162, that corresponds to a whole number of pump activations 158 which occurred at time 161, and a fraction of the stroke volume 160 of the pump 10 which occurred after time 161, but before time 162, the time at which the next whole number pump activation occurs. Immediately upon receiving instructions to deliver a demand or automatic dose, the microprocessor 120 calculates in real-time the amount of undelivered fluid which corresponds to a whole number of pump activations or stroke volumes 158. The volume 158 is delivered at time 156. A volume equal to the amount of volume 158, however, normally gets delivered at time 161. Since time 156 is longer than time 161, the effective rate of delivery of volume 158 is decreased, as is represented in FIG. 3A.

The area 160 corresponds to the fractional volume of undelivered fluid which is immediately due to the patient. In the preferred embodiment, the interval to the next pump activation 162 is shortened so that the undelivered fractional activation volume of fluid 160 is included as part of the volume 163.

Because the demand or automatic dose interrupted the delivery of fluid at the basal rate 140, FIG. 3B illustrates a volume due at time 156 of less than two units of fluid. The undelivered fractional activation volume 160 is added to the volume due as 160' at the time interval 162.

In the preferred embodiment, the un-delivered fluid 158, 160 is delivered to the patient as quickly as possible so as to prevent under-delivery in the event the pump 10 is stopped prematurely. After the fractional amount of fluid 160 is delivered to the patient in the shortened interval 163, the new effective rate 164 is calculated by determining the time interval 166 for achieving the desired rate.

The rate change at time 170 corresponds to a decrease in the effective rate 164 occurring at a time which leaves an undelivered volume of fluid which corresponds to a whole number of pump activations 172 and a fraction of the stroke volume 174 of the pump 10. Also, because the anticipated volume due has not changed, the slope of the line formed by areas 172 and 174 in FIG. 3B is the same as the slope of the prior two triangles (starting at time intervals 162 and 166). The microprocessor 120 calculates the volume of fluid corresponding to a whole number of pump activations or stroke volumes 172 and immediately delivers that fluid to the patient. As is illustrated in FIG. 3B, the undelivered volume of fluid 174 due, which corresponds to a fraction of a stroke volume, is added to the next pump activation as 174'.

FIGS. 4A–4D illustrate a flow chart showing the preferred method and system for delivering fluid according to a basal rate, and any active or demand doses. If a dose is beginning or ending, a new calculation 200 is performed. The information describing the type of rate change is saved 202 in memory 122. A new rate is calculated by summing the basal rate and any active doses 204. The total rate is first set to zero 206. If there is a basal rate 208, the basal rate is added to the total rate 210. If there is an automatic dose 212, the volume of the automatic dose is divided by the duration to determine a rate which is added to the total rate 214. If there is a demand dose 216, the total volume of the demand dose is divided by the duration of the demand dose to calculate a rate which is added to the total rate 218.

Figure 4A:
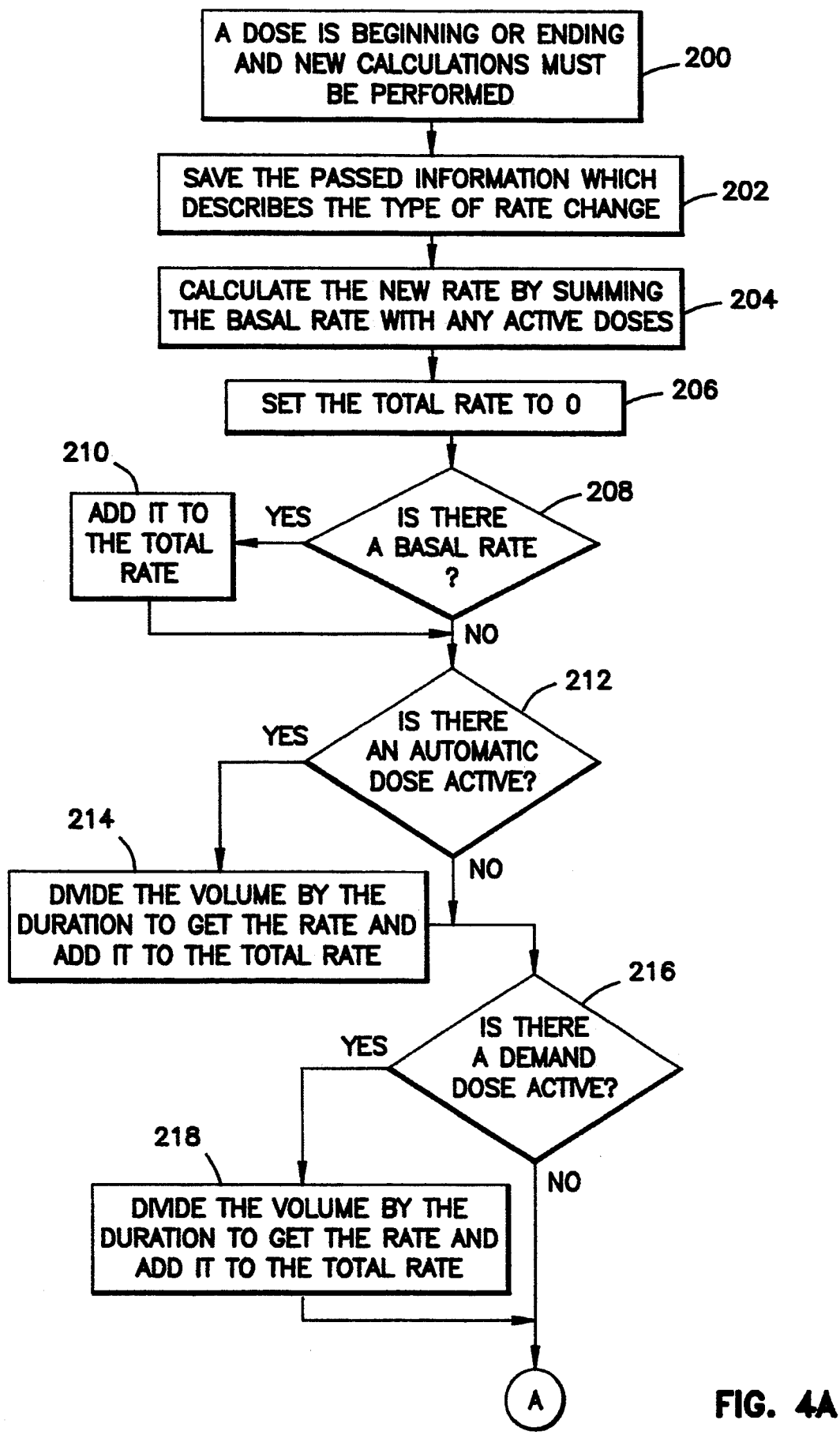
FIGS. 4A–4D illustrate a flow chart showing the preferred method and system for controlling the preferred drug delivery pump.
Figure 4B:
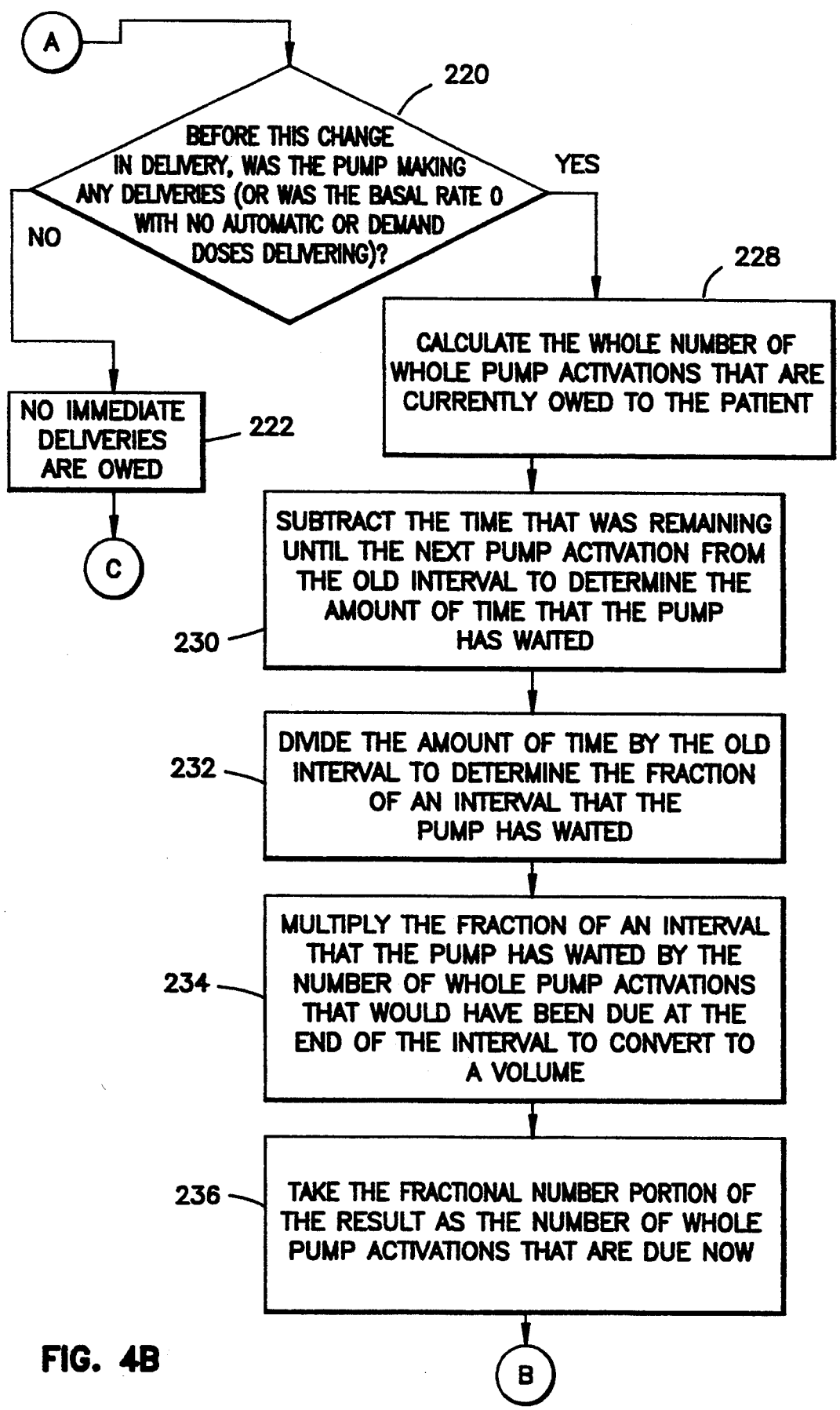

Turning now to FIG. 4B, the system then determines whether the pump was making any deliveries 220 prior to the rate change 204. If no immediate deliveries are owed 222, the system determines if the new rate 204 is greater than zero 224 and a new interval 226 is calculated for the delivery volume.

Alternatively, if the pump 10 was making a delivery 220 at the time that the new rate 204 is calculated, the system determines the whole number of pump activations 228 which are owed to the patient. The whole number of pump activations owed to the patient 228 is calculated by subtracting the time that was remaining until the next pump activation from the old interval to determine the amount of time that the pump has waited 230. The amount of time that the pump has waited is divided by the old interval to determine a fraction of an interval that the pump has waited 232. The fraction of an interval that the pump has waited is multiplied by the number of pump activations that would have been due at the end of the interval in order to convert the time into a volume of fluid 234. The whole number portion of the result is taken as the number of pump activations that are currently due to the patient. In the preferred embodiment, these whole pump activations are immediately delivered to the patient in order to deliver the required volume of fluid as close as possible to the time it was scheduled for delivery.

Figure 4C:
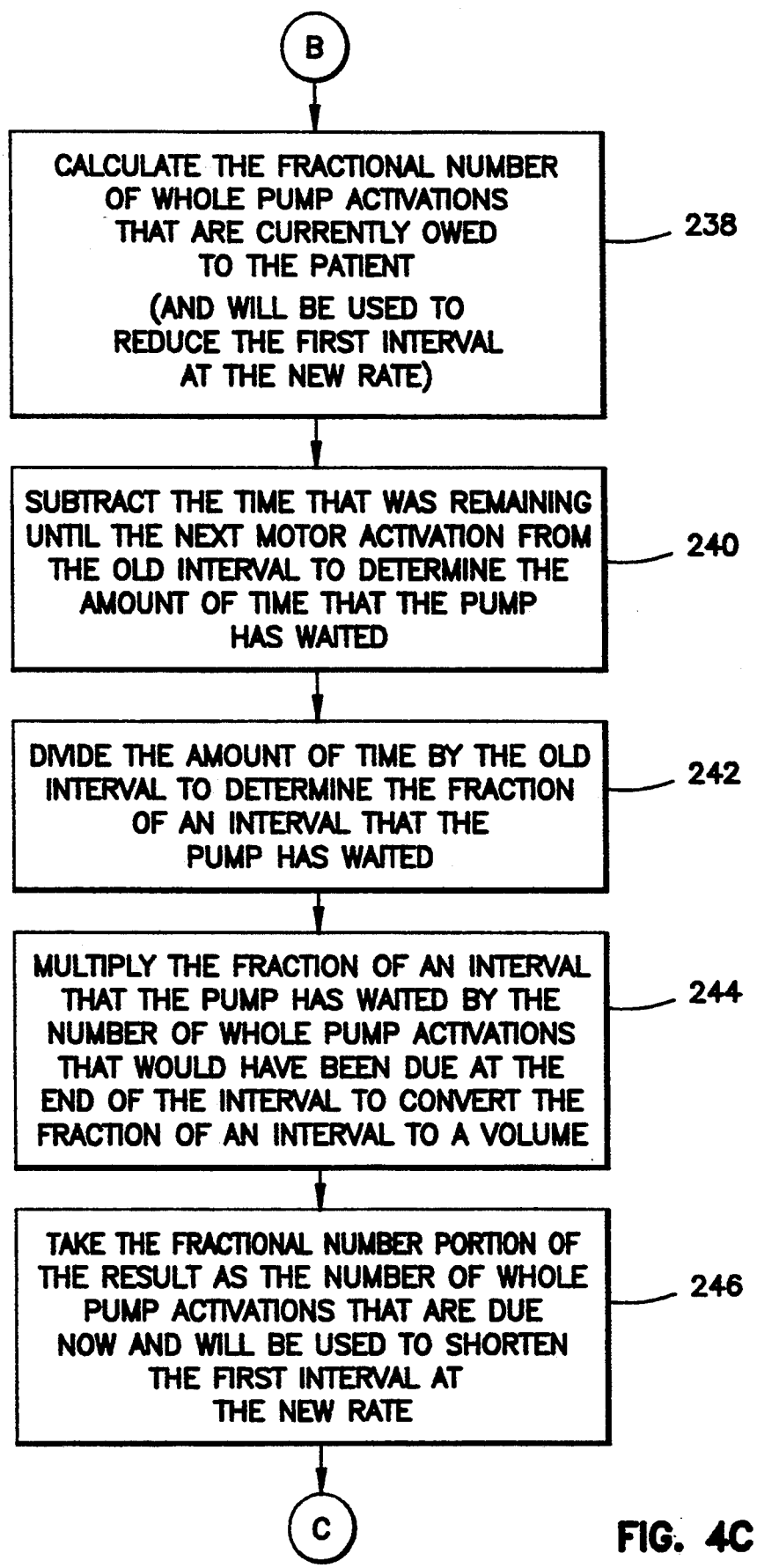

Turning now to FIG. 4C, the system calculates the fractional number of pump activations that are currently owed to the patient 238. The time remaining until the next motor activation is subtracted from the old interval to determine the amount of time the pump has waited 240. The amount of time that the pump has waited is divided by the old interval to determine the fraction of an interval that the pump has waited 242. The fraction of an interval that the pump has waited is multiplied by the number of pump activations that would have been due at the end of the interval to convert the fraction of an interval to a volume 244. The fractional portion of the result is taken as the number of pump activations that are due 246. The fractional volume of fluid which is due to the patient is used to shorten the first interval at the new rate. This fractional volume of fluid is preferably delivered immediately after the whole number of pump activations due to the patient are delivered so that fluid is delivered as close to the scheduled time as possible.

Figure 4D:
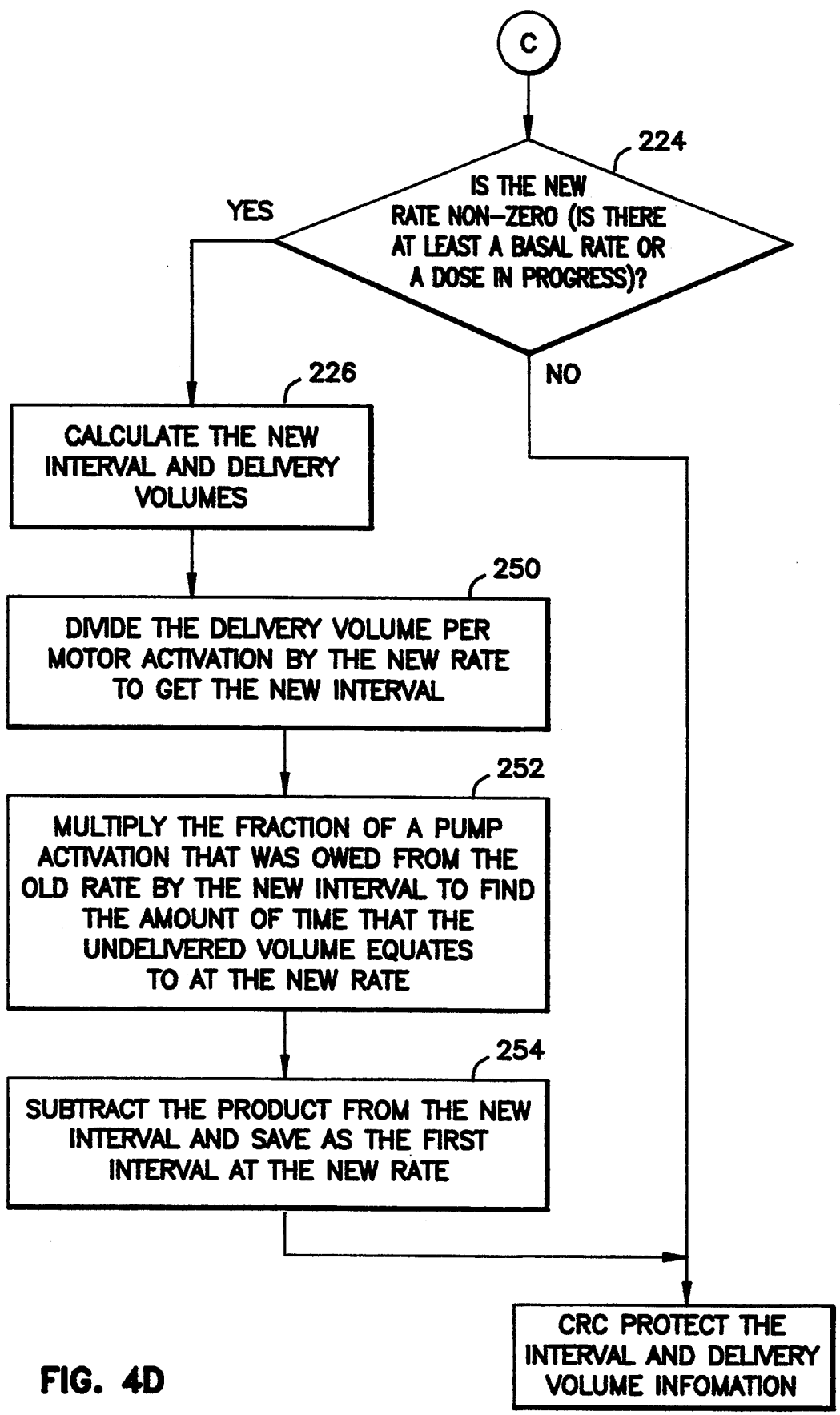

Turning now to FIG. 4D, the step of calculating the new interval and delivery volumes 226 preferably includes dividing the delivery volume per motor activation by the new rate to get a new interval 250. The fraction of the pump activation that was owed from the old rate is multiplied by the new interval to find the amount of time that the undelivered volume equates to at the new rate 252. A product from the new interval is subtracted and saved as the first interval at the new rate 254.

Other modifications of the invention will be apparent to those skilled in the art in view of the foregoing descriptions. These descriptions are intended to provide specific examples of embodiments which clearly disclose the present invention. Accordingly, the invention is not limited to the described embodiments or to the use of specific elements, dimensions, materials or configurations contained therein. All alternative modifications and variations of the present invention which fall within the spirit and broad scope of the appended claims are covered.

What is claimed is:

1. A programmable infusion pump for administering fluid to a patient at multiple programmable rates and for calculating an effective rate on a real-time basis, the pump having a motor with a stroke volume corresponding to a discrete volume of fluid for each pump activation for delivering a volume of fluid during an infusion cycle, comprising:

input means for receiving, (i) a basal infusion rate corresponding to a time interval between basal pump activations, (ii) an automatic dose having a start time, an automatic dose volume, and a duration, and (iii) a demand dose having a start time, a demand dose volume and a duration;

means for identifying the start time of an automatic dose, including means for calculating a rate for the automatic dose;

means for detecting the start time of a patient activated demand dose, including means for calculating a rate for the demand dose;

means for calculating the effective rate corresponding to a time interval between pump activations, comprising the sum of the basal rate and any automatic and demand dose rates, the means for calculating including means for identifying a start time for the effective rate;

means for determining any undelivered volume of fluid which is scheduled for delivery prior to the start time of the effective rate, including means for delivering the portion of the undelivered volume of fluid corresponding to a whole number of stroke volumes;

means for determining any portion of the undelivered volume of fluid which is a fraction of the stroke volume of the motor;

means for altering at least one of the time intervals subsequent to the new effective rate to include the fractional portion of the undelivered volume; and pump means for administering the fluid to the patient according to the effective rate.

2. The apparatus of claim 1 wherein automatic doses are scheduled prior to its start time.

3. The apparatus of claim 1 wherein the means for altering at least one of the time intervals comprises shortening the time interval subsequent to the delivery of the undelivered volume of fluid corresponding to a whole number of stroke volumes.

4. The apparatus of claim 1 wherein the means for altering at least one of the time intervals at the effective rate includes shortening the time interval to achieve an increased rate.

5. The apparatus of claim 1 wherein the means for delivering the portion of the undelivered volume of fluid corresponding to a whole number of stroke volumes delivers said undelivered volume at the beginning of the effective rate.

6. The apparatus of claim 1 wherein the means for determining any undelivered volume of fluid which is scheduled for delivery prior to the start time of the effective rate comprises means for determining any undelivered volume of fluid which is scheduled for delivery during the time interval between the start of the pump activation prior to the effective rate and the start time for the effective rate.

7. The apparatus of claim 1 further comprising means for limiting patient access to the input means.

8. The apparatus of claim 7 wherein the means for limiting patient access further comprises a lockout time which corresponds to a minimum time interval between automatic or demand doses.

9. The apparatus of claim 8 wherein the pump further comprises means for generating an audio and/or visual alarm when the patient has chosen a start time for an automatic or demand dose which causes the automatic or demand dose to fall within the lockout time.

10. The apparatus of claim 1 further comprising means for limiting the patient's ability to change the automatic or demand dose volumes.

11. The apparatus of claim 1 wherein the input means further comprises means for changing and stopping an automatic and demand dose at any time during fluid administration.

12. The apparatus of claim 1 wherein the pump further comprises means for generating an audio and/or visual alarm when the patient attempts to program the delivery of a volume of fluid which exceeds the capacity of the pump.

13. The apparatus of claim 1 wherein the pump further comprises means for generating an audio and/or visual alarm when the patient requests a demand dose while a demand dose is already in progress.

14. A method for administering fluid to a patient at multiple programmable rates and for calculating an effective rate on a real-time basis using a programmable infusion pump, the pump having a motor with a stroke volume corresponding to a discrete volume of fluid for each pump activation for delivering a volume of fluid during an infusion cycle, comprising the steps of:

providing input means for receiving, (i) a basal infusion rate corresponding to a time interval between basal pump activations, (ii) an automatic dose having a start time, an automatic dose volume, and a duration, and (iii) a demand dose having a start time, a demand dose volume and a duration;

identifying the start time of an automatic dose, including calculating a rate for the automatic dose;

detecting the start time of a patient activated demand dose, including calculating a rate for the demand dose;

calculating an effective rate corresponding to a time interval between pump activations comprising the sum of the basal rate and any automatic and demand dose rates, the step of calculating including identifying a start time for the effective rate;

determining any undelivered volume of fluid which is scheduled for delivery prior to the start time of the effective rate, including delivering the portion of the undelivered volume of fluid corresponding to a whole number of stroke volumes;

determining any portion of the undelivered volume of fluid which is a fraction of the stroke volume of the motor;

altering at least one of the time intervals at the effective rate to include the fractional portion of the undelivered volume; and administering the fluid to the patient with the programmable infusion pump according to the effective rate.

15. The method of claim 14 wherein the step of altering at least one of the time intervals comprises shortening the time interval subsequent to the delivery of the undelivered volume of fluid corresponding to a whole number of stroke volumes.

16. The method of claim 14 wherein the step of altering at least one of the time intervals at the effective rate includes shortening the time interval to achieve an increased rate.

17. The method of claim 14 wherein the step of delivering the portion of the undelivered volume of fluid corresponding to a whole number of stroke volumes comprises delivering said undelivered volume of fluid at the beginning of the effective rate.

18. The method of claim 14 wherein the step of determining any undelivered volume of fluid which is scheduled for delivery prior to the start time of the effective rate comprises determining any undelivered volume of fluid which is scheduled for delivery during the time interval between the start of the pump activation prior to the effective rate and the start time for the effective rate.

* * * * *